US008642303B2

(12) United States Patent
Benson et al.

(10) Patent No.: US 8,642,303 B2
(45) Date of Patent: *Feb. 4, 2014

(54) PROCESS FOR ALCOHOLIC FERMENTATION OF LIGNOCELLULOSIC BIOMASS

(75) Inventors: Robert Ashley Cooper Benson, North Bay (CA); Regis-Olivier Benech, Chatham (CA)

(73) Assignee: GreenField Specialty Alcohols Inc., Toronto, Ontario (CA)

( * ) Notice: Subject to any disclaimer, the term of this patent is extended or adjusted under 35 U.S.C. 154(b) by 837 days.

This patent is subject to a terminal disclaimer.

(21) Appl. No.: 12/644,935

(22) Filed: Dec. 22, 2009

(65) Prior Publication Data

US 2010/0159552 A1     Jun. 24, 2010

Related U.S. Application Data

(60) Provisional application No. 61/140,451, filed on Dec. 23, 2008.

(51) Int. Cl.
| | | |
|---|---|---|
| *C07K 1/00* | (2006.01) | |
| *C12P 1/00* | (2006.01) | |
| *C12P 7/00* | (2006.01) | |
| *C12P 7/02* | (2006.01) | |
| *C12P 7/06* | (2006.01) | |
| *C12P 7/10* | (2006.01) | |
| *D21C 1/00* | (2006.01) | |

(52) U.S. Cl.
USPC ............. 435/165; 435/41; 435/132; 435/155; 435/161; 435/267; 435/273; 435/277

(58) Field of Classification Search
None
See application file for complete search history.

(56) References Cited

U.S. PATENT DOCUMENTS

| | | | |
|---|---|---|---|
| 7,455,997 B2 | 11/2008 | Hughes | |
| 8,287,651 B2 * | 10/2012 | Benson et al. | 127/37 |
| 8,293,508 B2 * | 10/2012 | Lantero et al. | 435/161 |

| | | |
|---|---|---|
| 2008/0131947 A1 | 6/2008 | Wicking |
| 2008/0193991 A1 | 8/2008 | Allen et al. |
| 2009/0093027 A1 | 4/2009 | Balan et al. |

OTHER PUBLICATIONS

Sedlak et al., "Production of Ethanol from Cellulosic Biomass Hydrolysates Using Genetically Engineered Saccharomyces Yeast Capable of Cofermenting Glucose and Xylose", Journal of Applied Biochemistry and Biotechnology, Mar. 2004, pp. 403-416, vol. 114, No. 1-3, Humana Press Inc.
Kadam et al., "Development of a low-cost fermentation medium for ethanol production from biomass", Journal of Applied Microbiology and Biotechnology, Jun. 1997, pp. 625-629, Springer Berlin / Heidelberg.
Srinivasan et al., "Fiber Separated from Distillers Dried Grains with Solubles as a Feedstock for Ethanol Production", Cereal Chemistry, Nov./Dec. 2007, pp. 563-566, vol. 84(6).
Taherzadeh et al., "Pretreatment of Lignocellulosic Wastes to Improve Ethanol and Biogas Production: A Review", International Journal of Molecular Sciences, Sep. 1, 2008, pp. 1621-1651, vol. 9.
White et al., "Bioconversion of Brewer's Spent Grains to Bioethanol", FEMS Yeast Research, Jun. 10, 2008, pp. 1175-1184, vol. 8(7), Blackwell Publishing Ltd.
Gunasekaran et al., "Ethanol Fermentation Technology—Zymomonas mobilis", Current Science, Jul. 10, 1999, pp. 56-68, vol. 77(1).
International Application No. PCT/CA2009/001844, International Search Report dated Mar. 17, 2010.

* cited by examiner

*Primary Examiner* — Debbie K Ware
(74) *Attorney, Agent, or Firm* — Borden Ladner Gervais LLP

(57) ABSTRACT

A process for the production of ethanol wherein a hydrolyzed lignocellulosic biomass is fermented in the presence of a stillage residue. The fermentation of cellulosic hydrolysates is improved by adding prior to and/or during fermentation a stillage residue side stream from a corn starch-to-ethanol process as a nutrient source for the yeast organisms used in the fermentation. Stillage residues from the grain dry mill ethanol producing process, including the whole stillage, wet cake, thin stillage, and/or syrup are added to assist as a nitrogen and nutrient source for the fermentive processes. The stillage residue is produced by any grain-to-ethanol process.

14 Claims, 4 Drawing Sheets

PROCESS FOR ALCOHOLIC FERMENTATION OF LIGNOCELLULOSIC BIOMASS

CROSS-REFERENCE TO RELATED APPLICATIONS

This application claims the benefit of priority from U.S. Provisional Patent Application No. 61/140,451 filed Dec. 23, 2008, which is incorporated herein by reference in its entirety.

FIELD OF THE INVENTION

The present invention generally relates to the production of ethanol from biomass and is particular to an improved process for alcoholic fermentation of lignocellulosic biomass.

BACKGROUND OF THE INVENTION

World energy consumption is predicted to increase 54% between 2001 and 2025. Considerable effort is being directed towards the development of sustainable and carbon neutral energy sources to meet future needs.

Biofuels are an attractive alternative to current petroleum-based fuels, as they can be utilized as transportation fuels with little change to current technologies and have significant potential to improve sustainability and reduce greenhouse gas emissions.

Ethanol is a liquid alcohol made up of oxygen, hydrogen and carbon and is obtained by the fermentation of sugar or converted starch contained in corn grains or converted cellulose from other agricultural or agri-forest feedstocks. The fermentation broth is distilled and dehydrated to create a high-octane, water-free alcohol. Ethanol is blended with gasoline to produce a fuel which has environmental advantages when compared to gasoline, and can be used in gasoline-powered vehicles manufactured since the 1980's. Most gasoline-powered vehicles can run on a blend consisting of gasoline and up to 10% ethanol, known as "E-10".

In North America the feedstock is primarily corn grain, while in Brazil sugar cane is used. However, there are disadvantages to using potential food or feed plants to produce ethanol and the availability of such feedstock is limited by the overall available area of suitable agricultural land.

The term cellulosic ethanol, describes ethanol that is manufactured from lignocellulosic biomass. There are many different sources of lignocellulosic biomass. The sources may be grouped into four main categories: (1) wood residues (including sawmill and paper mill rejects), (2) municipal paper waste, (3) agricultural residues (including corn stover, corn cobs and sugarcane bagasse), and (4) dedicated energy crops (mostly composed of fast growing tall, woody grasses such as switch grass and Miscanthus).

Lignocellulosic biomass is composed of three primary polymers that make up plant cell walls: Cellulose, hemicellulose, and lignin. Cellulose fibers are locked into a rigid structure of hemicellulose and lignin. Lignin and hemicelluloses form chemically linked complexes that bind water soluble hemicelluloses into a three dimensional array, cemented together by lignin. The complexes cover cellulose microfibrils and protect them from enzymatic and chemical degradation. These polymers provide plant cell walls with strength and resistance to degradation. This makes them a challenge to use as substrates for biofuel production.

Production of ethanol from cellulose via fermentation is a complex process that starts with feed preparation and is followed by biochemical conversion and distillation.

Delivery of biomass starts with selective harvesting, transportation, storing and reducing steps. Biochemical conversion of lignocellulosic biomass to ethanol involves four steps: (1) High pressure treatment of raw lignocellulosic biomass to make the complex polymers more accessible to enzymatic breakdown; (2) production and application of special enzyme preparations (cellulases and hemicellulases) that hydrolyze pretreated plant cell-wall polysaccharides to a mixture of simple sugars; (3) fermentation, mediated by bacteria or yeast, to convert these sugars to ethanol; and (4) ethanol distillation and dehydration.

One variable in the composition of biomass that affects the conversion to energy is lignin. There is evidence that lignin inhibits the process of breaking down biomass to sugars for fermentation. Lignin and some soluble lignin derivatives inhibit enzymatic hydrolysis and fermentation processes. Thus, it is desirable to use a lignocellulosic feedstock which is low in lignin. The lignin content of corncobs, (less than 8% by weight) is low, which would make this a good biomass feedstock for the production of ethanol. However the hemicellulose content of corncobs is high, about 30 to 40% of the total dry matter. Moreover, much of the hemicellulose is acetylated which means that breakdown and liquefaction of the hemicellulose leads to the formation of acetic acid. This is a problem, since the acid is a powerful inhibitor of the ethanol fermentation process. It remains in the pretreated biomass and carries through to the hydrolysis and fermentation steps.

Diverse techniques have been explored and described for the pretreatment of size-reduced biomass with the aim of producing a substrate that can be more rapidly and efficiently hydrolyzed to yield mixtures of fermentable sugars.

These approaches have in common the use of conditions and procedures which greatly increase the surface area to which aqueous reactants and enzymes have access. In particular, increasing the percentage of the cellulosic materials that are opened up to attack decreases the time needed to hydrolyze the cellulose polymers to simple sugars. However, pretreatments of lignocellulosic biomass, such as steam explosion, may result in extensive cellulose breakdown and, to a certain extent, to the degradation of hemicellulose. This results in the production of acetic acid and furfural. Some pretreatment methods employ hydrolytic techniques using mineral acids (hemicellulose hydrolysis) and alkalis (lignin removal).

Pretreatments involving mineral acids (including $SO_2$) primarily solubilize the hemicellulose component of the feedstock while the use of organic solvents and alkalis tends to co-solubilize lignin and hemicellulose.

The resulting product streams (called pre-hydrolysates) are usually separated thereafter into liquid and solid (cellulose) phases. If no separation or detoxification is included in the process, a complex mixture of toxic compounds such as acetic acid and furans will be carried forward to the hydrolysis and fermentation steps. The inhibitory compounds significantly reduce enzyme performance, biocatalyst growth, rates of sugar metabolism, and final ethanol titer due to incomplete conversion of the glucose to ethanol.

The mentioned inhibitors are generally removed through a dedicated step to detoxify pretreatment hydrolysates before fermentation. Detoxification requires additional equipment, e.g. solid-liquid separation, storage tanks, and may also require the addition of chemicals such as calcium hydroxide for over liming, acid for neutralization before fermentation and high yeast nutrient loads, hence added process complexity.

This additional process complexity results in increased capital equipment and operating costs. Therefore, it would be desirable to avoid the need to detoxify completely biomass prehydrolysate prior to the enzymatic hydrolysis and fermentation steps.

Fermentation of sugars by yeast (e.g. *Saccharomyces cerevisiae*) is the most common method for converting sugars released from biomass feedstocks into fuels, such as ethanol. Yeasts are living organisms, unicellular fungi that need carbon, nitrogen, vitamins, and minerals for growth and reproduction. If compared to corn grain mash, lignocellulosic hydrolysates are not nutritionally balanced for yeast and most need to be fortified with additional macronutrients like nitrogen.

Nitrogen is an essential element needed to avoid sluggish and stuck fermentation. Nitrogen deficiency will cause problems in four fundamental ways. The first three are related to each other as follows: (1) protein synthesis is limited; (2) cell count is limited because the proteins are the bricks used to built new cells, and (3) fermentation kinetics are slowed down due to the reduced cell count. The fourth manner in which nitrogen deficiencies can cause sluggish fermentation is through a decrease in the efficiency of the sugar transporters in the yeast cell membrane, causing a significant decrease in fermentation kinetics at the cellulose level.

Yeast accessible nitrogen is composed of two portions, organic or assimilable nitrogen and inorganic nitrogen (ammonia). Advantageous fermentation broths contain a balance of yeast available nitrogen from both assimilable amino nitrogen and inorganic nitrogen. Therefore, the fermentation step typically requires external nutrient supplementation.

Another major barrier in the efficient use of biomass-derived sugars is the lack of industrial grade yeast that can grow and function optimally in challenging, stressful environments created by lignocellulosic biomass pretreatments as discussed above.

During the fermentation of a detoxified biomass hydrolysate, a significant fraction of available sugar may be diverted by the yeast away from ethanol production to glycerol and succinic acid production. Glycerol production in the yeast is linked to acid, ethanol, and temperature induced stress conditions. The synthesis of glycerol occurs in response to osmotic stress and therefore likely has an essential role in cell viability.

Although yeasts with improved properties such as elevated ethanol and temperature tolerances have been genetically engineered, such strains are not yet used widely by the fuel ethanol industry.

All of the above mentioned problems contribute to the elevated capital cost and operating cost of lignocellulosic ethanol production by reducing product yields, and increasing water volumes that must be handled as part of relatively dilute product streams.

Ethanol production from glucose or from grain or corn starch is now a mature industry. Production of fuel ethanol from sugars present in lignocellulosic biomass, however, remains challenging with many opportunities for improvement.

Thus, improving the throughput and reducing the costs associated with ethanol production from lignocellulosic biomass, is critical to the establishment of a viable industry.

SUMMARY OF THE INVENTION

It is now an object of the present invention to provide a process which overcomes at least one of the above disadvantages.

The inventors of the present application have realized that process integration of cellulosic ethanol production with residue streams from an existing starch-based process would reduce both capital and operating costs, which remain high by comparison with those of corn.

The inventors have further discovered that savings in capital and operating costs can be realized by developing improved cellulose to ethanol processes wherein the fermentation of cellulosic hydrolysates is improved by adding prior to and/or during fermentation a residue side stream or stillage residue from a corn starch-to-ethanol process as a nutrient source for the yeast organisms used in the fermentation. This nutrient source not only improves the fermentation rate and efficiency, but also improves the resistance of the yeast organisms to acidic and/or other impurities or inhibitors in the cellulosic hydrolysates. These impurities and inhibitors may have been created or added during cellulose pretreatment and cellulose hydrolysis. Using a nutrient stream from a corn to ethanol process to fortify lignocellulosic hydrolysates even provides the possibility of carrying out the fermentation process with only partial washing, limited detoxification or pH adjustment of the cellulose hydrolysates, or even without any washing, detoxification, or pH-adjustment. All of this is achieved by simply adding prior and/or during fermentation a side stream or stillage residue from a grain starch-to-ethanol process.

In one preferred aspect, the invention provides a cellulose-to-ethanol process wherein fermentation of cellulosic hydrolysates derived from ligno-cellulosic biomass can be carried out with full washing and detoxification, partial washing, detoxification or pH-adjustment of the cellulosic hydrolysates, or without any prior washing or detoxification of the steam explosion pretreated biomass hydrolysates.

In a further preferred aspect, the invention provides a cellulose-to-ethanol process wherein stillage residue streams from a grain or corn grain starch-to-ethanol dry mill process are added during fermentation to reduce the need for pH adjustment or external nutrient supplementation.

In one aspect, the present invention resides in a process for the production of ethanol, the process comprising the step of fermenting a hydrolyzed lignocellulosic biomass in the presence of a stillage residue, the stillage residue is produced by a whole grain starch-to-ethanol process.

In a preferred aspect, the stillage residue is selected from the group consisting of whole stillage, thin stillage, wetcake, syrup, and any combination thereof.

In a preferred aspect, the process further comprises a propagation step whereby yeast is conditioned and grown prior to the step of fermentation.

In a preferred aspect, the hydrolyzed lignocellulosic biomass is produced by acid pre-treatment wherein the acid catalyst is a mineral acid or a carboxylic acid.

In a preferred aspect, the hydrolyzed lignocellulosic biomass is selected from the group consisting of agricultural residues, purpose grown crops, woody biomass, and any combination thereof.

In a preferred aspect, the hydrolyzed lignocellulosic biomass is obtained from corn cobs.

In a preferred aspect, the ethanol is produced by fermentation with a ethanologenic organism.

In a preferred aspect, the ethanologenic organism is a prokaryotic organism.

In a preferred aspect, the ethanologenic organism is selected from the group consisting of *Escherichia coli, Klebsiella oxytoca*, and *Zymomonas mobilis, Clostridium thermocellum*.

In a preferred aspect, the ethanologenic organism is a eukaryotic organism.

In a preferred aspect, the eukaryotic organism is selected from the group consisting of Saccharomyces cerevisia, Pichia stipitis.

In another aspect, the present invention resides in a process comprising the step of propagating yeast in the presence of a stillage residue from a whole grain starch-to-ethanol process.

In a preferred aspect, the stillage residue is selected from the group consisting of whole stillage, thin stillage, wetcake, syrup, and any combination thereof.

In another aspect, the present invention resides in a process for the production of cellulosic ethanol from lignocellulosic biomass, comprising the steps of: pretreating the lignocellulosic biomass to decompose the lignocellulosic biomass into fibrous solids; hydrolyzing the fibrous solids with enzymes to produce cellulose sugars; and fermentating the cellulose sugars in the presence of a stillage residue from a whole grain starch-to-ethanol dry mill process.

In a preferred aspect, the stillage residue is selected from the group consisting of whole stillage, thin stillage, wetcake, syrup, and any combination thereof.

In a preferred aspect, the step of pretreating the lignocellulosic biomass includes process conditions including the step of exposing the lignocellulosic biomass to steam in a reaction vessel at an elevated temperature and reaction pressure for a preselected exposure time, and releasing the reaction pressure for explosive decomposition of the lignocellulosic bioimass.

In a preferred aspect, the elevated temperature is in the range of 190-210° Celsius, the reaction pressure is between 190 to 275 psig, and the preselected exposure time is between 3 to 10 minutes.

In a preferred aspect, the elevated temperature is 205 degrees Celsius, the reaction pressure is 235 psig, and the preselected exposure time is 8 minutes.

In a preferred aspect, the pressure is released within less than 1000 milliseconds.

In a preferred aspect, the pressure is released within 300 milliseconds.

In a preferred aspect, the process conditions are selected for the achievement of a severity index of 3.9 to 4.1.

In a preferred aspect, the severity index is 4.0.

In a preferred aspect, the enzymatic hydrolysis is carried out at 10-30% consistency, and at a temperature of 40-60° Celsius and a pH 4.5 to 5.5.

In a preferred aspect, the fermentation step is carried out at 10-30% consistency, 30-37° C. and a pH of 5.2 to 5.9.

In a preferred aspect, the enzymatic hydrolysis of solids generated during the pressure release steps is carried out at a temperature of 50° C., pH 5.0 until completion.

In a preferred aspect, the fermentation step is carried out at a temperature of 35° C., and at a pH of 5.3 until completion.

In a preferred aspect, the process includes a process arrangement step for step of collecting and processing fermentation products for distilling fuel grade ethanol.

In a preferred aspect, the process arrangement step for distilling fuel grade ethanol includes a distillation portion, a condensation and dehydration portion, a separation and drying portion and an evaporation portion.

In a preferred aspect, the process arrangement produces hot ethanol vapor and thin stillage.

BRIEF DESCRIPTION OF THE DRAWINGS

Other objects and advantages of the invention will become apparent upon a reading of the detailed description and upon reference to the drawings in which.

DETAILED DESCRIPTION OF PREFERRED EMBODIMENTS

Figure 1:
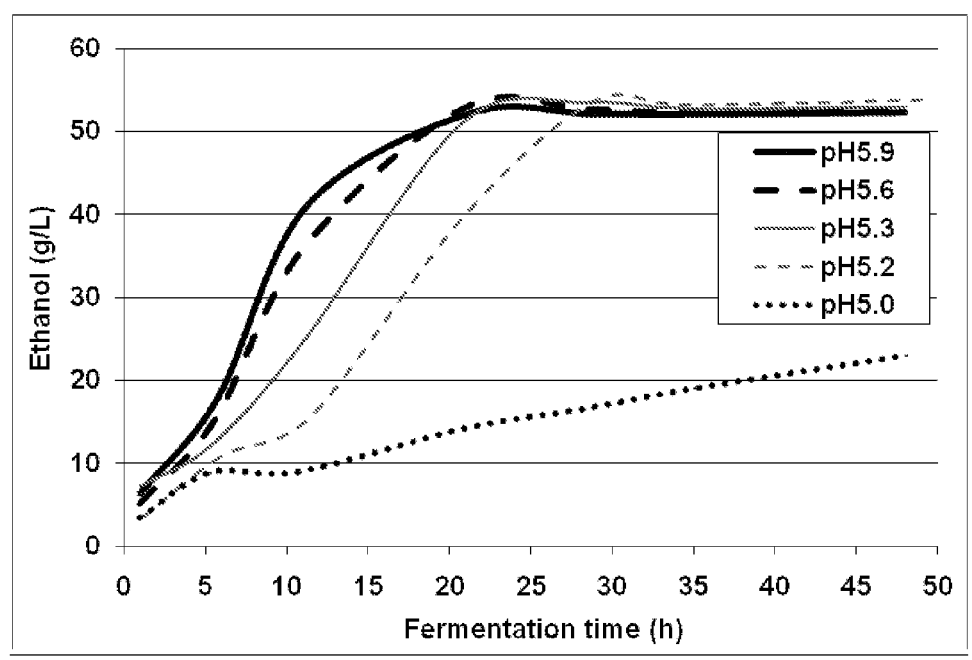
FIG. 1 shows the effect of pH on the fermentability of unwashed, undetoxified corncob hydrolysate from steam explosion pretreatment in the absence of external nutrient supplementation.

Before explaining the present invention in detail, it is to be understood that the invention is not limited to the preferred embodiments contain herein. The invention is capable of other embodiments and of being practiced or carried out in a variety of ways. It is to be understood that the phraseology and terminology employed herein are for the purpose of description and not of limitation.

The abbreviations used in figures and tables have the following meaning:

h, hours
g/l, gram per liter
ml, milliliter
DM, Dry matter
t90%, time (hours) to reach 90% of the maximum theoretical conversion of glucose to ethanol Table 1 shows the impact of pH on fermentation rates;
Tables 2A and 2B show the effect of pH adjustment on the cost of pH adjustment chemical (aqueous ammonia) used in unwashed, undetoxified corncob prehydrolysates hydrolysis and fermentation;
Table 3 shows the impact of commercial yeast nutrient load on glucose to ethanol rates;
Tables 4A and 4B show composition analysis of alternative yeast nutrients; and
Table 5 shows the impact of nutrient sources and loads on fermentation rates of unwashed, undetoxified corncob hydrolysates when the fermentation is carried out at a low load of pH adjustment chemical (pH 5.3).

The invention is directed to ethanol from biomass processes and especially to cellulose fermentation processes. In particular, the invention is directed to processes intended to achieve fermentation of cellulosic hydrolysates which include one or more acidic or other impurities or inhibitors of the yeast used in the fermentation step. Preferably, the invention provides a process which partially or fully obviates the step of washing or detoxification of a lignocellulosic hydrolysate prior to fermentation.

In a common dry mill grain or corn grain ethanol producing plant, the ethanol is removed from the fermented mash in a distillation column. After the ethanol is removed, the remaining residue is removed as stillage residue. The stillage residue which is not refined is known as whole stillage. The whole stillage can be run through a solid-liquid separation step producing a solid stream of residue, also known as wet cake, and a liquid stream of residue, also referred to as thin stillage.

The thin stillage can be further processed to increase the solids concentration by evaporation resulting in Condensed Distillers Solubles or Syrup. Typically the Syrup is mixed back with the separated solid stream or wet cake and fed to a rotary drum dryer to remove the remaining moisture. The resulting dry solids are typically referred to as Dried Distillers Grains and Solubles or "DDGS", and sold as animal feed. However, the inventors have discovered that the stillage residues from the grain dry mill ethanol producing process, including the whole stillage, wet cake, thin stillage, and/or syrup present a low cost protein and nitrogen nutrient source for fermentive processes.

Adding the stillage residue as a nutrient source in accordance with the invention can reduce the amount of pH adjustment chemical required and reduce or eliminate the need for expensive nutrient supplements.

This process of adding the stillage residue as a nutrient source can be used with any lignocellulose to ethanol producing process including those using corncob or other lingocellulosic material as the starting cellulosic material. In particular, this process also applies to ethanol producing processes including steps of cellulose pretreatment, and hydrolysis methods.

Hemicellulose is a heteropolymer or matrix polysaccharide which is present in almost all plant cell walls along with cellulose. While cellulose is crystalline, strong, and resistant to hydrolysis, hemicellulose has a random, amorphous structure with little strength. Hydrolysis of hemicellulose can be relatively easily achieved with acids or enzymes. Hemicellulose contains many different sugar monomers. For instance, besides glucose, hemicellulose can include xylose, mannose, galactose, rhamnose, and arabinose. Xylose is the monomer present in the highest amount.

While cellulose is highly desirable as a starting material for biochemical ethanol production, hemicellulose and most of its hydrolytic degradation products interfere with the downstream fermentation of glucose from cellulose. In particular, xylose derivatives and degradation products, and acetic acid, all of which are products of hemicellulose hydrolysis, are strong inhibitors of glucose fermentation.

EXAMPLE 1

Complete Enzymatic Digestion of Corncob Pre-Hydrolysates was Carried out with a Commercial Enzyme Product GC220 (Genencor) at 3.0% Load (w/w, DM), 50° C., and pH 5.0

The preferred enzymatic digestion conditions were found to be 10-30% consistency of the prehydrolysate, a temperature of 40-60° C. and a pH of 4.5-5.5.

Fermentations were carried out using Ethanol Red™, a commercial industrial grade C6-fermenting yeast from Fermentis (division of Lesaffre group), as a benchmark yeast. Yeast inoculation was carried out by adding 6.67 g dry yeast per kilogram of corncob hydrolysates leading to an average yeast population of $10^8$ cells/ml hydrolysate after rehydration.

The benchmark conditions for the fermentation experiments were 35° C., pH 5.9, using commercial nutrient (Goferm™, 8.3 g/kg corncob hydrolysates or 4.0% (w/w, DM) load). Preferred fermentation conditions were found to be a consistency of 10-30%, a temperature of 30-37° C. and a pH of 5.2 to 5.9.

Fermentations were carried out in 1-liter beakers. The key parameters used were fermentation rates and yield. Fermentation rates and yield of batch or continuous steam explosion pretreated corncob were assessed with respect to pH adjustment chemical usage and yeast nutrient needs.

pH adjustment of unwashed, undetoxified hydrolyzed corncobs prehydrolysate was carried out prior to fermentation using different quantities of liquid ammonia (30%, w/w). Starting pH's ranged from 5.0 to 5.9.

Yeast nutrient needs were first evaluated using different loads of a commercial yeast nutrient (Goferm) with respect to fermentation rates and yield. The performance of Goferm was used as a benchmark for the screening and identification of industrial side streams or stillage residues.

The industrial side streams or stillage residues evaluated were whole and thin stillage, wet cake and syrup from a corn starch-to-ethanol dry mill as well as heavy steep water from a wet mill.

Glucose, xylose, ethanol, glycerol and carboxylic acid concentrations were determined by HPLC analysis. Quantification of soluble products from pretreatment, enzymatic hydrolysis and fermentation were carried out by HPLC analysis. Target molecules were monitored to determine the relative contents of cellulose and downstream inhibitors in the prehydrolysate obtained. The target molecules were sugar monomers such as glucose and xylose as well as toxic compounds such as different carboxylic acids, namely acetic acid, succinic acid and lactic acid and degradation products of carbohydrates such as glycerol, HMF and furfural as well as ethanol.

Composition analyses of commercial yeast nutrient and industrial side streams or stillage residuess were performed by an external laboratory (DairyOne). The overall hydrolysis and fermentation time of the batch-pretreated corncobs was generally less than 100 hours in total.

The summary results of the test fermentation series are plotted in FIGS. 1 to 4 and Tables 1 to 5.

As shown in FIG. 1, fermentation of unwashed, undetoxified corncob pre-hydrolysates can be accomplished at reasonable ethanol concentrations in reasonable time at pH values higher than pH 5.6 in absence of nutrient. Glucose from corncob hydrolysates can be converted to ethanol with a yield of 92% of the theoretical maximum, using a commercial industrial grade C6-fermenting yeast. An ethanol concentration of 5.4% (w/v) can be reached in 23 hours to 40 hours.

Table 1 shows that lower pH in fermentation of corncob is associated with a slowdown of fermentation even in the presence of a high load of commercial yeast nutrients. The time to reach 90% of the maximum theoretical glucose to ethanol conversion increased from 15 hours to 24 hours when the pH was reduced from 5.9 to 5.2.

Figure 2:
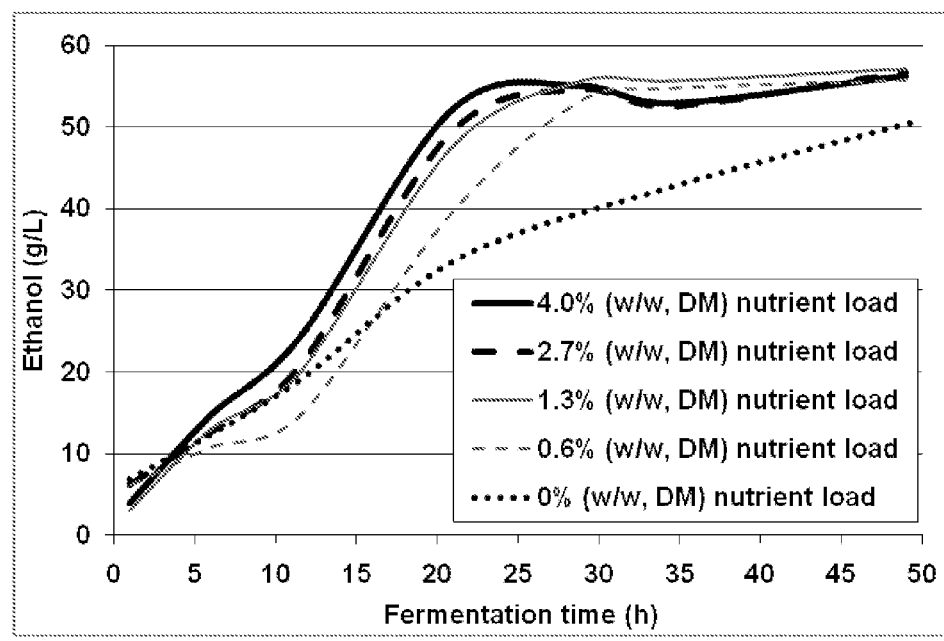
FIG. 2 shows the effect of commercial yeast nutrient load on the fermentability of unwashed, undetoxified corncob hydrolysate from steam explosion pretreatment, when the fermentation is carried out at a low load of pH adjustment chemical (pH 5.3)

FIG. 2 shows that the fermentation of hydrolysates had to be carried out with a minimum of 0.26% of commercial yeast nutrient, Goferm at pH of 5.3. Tables 2A and 2B show that the minimum ammonia usage for initial pH adjustment (pH 5.3) of corncob hydrolysates prior to fermentation was 10 ml ammonia (30%, w/w) per kilogram of corncob dry matter. This corresponds to 2.7 g of pure ammonia per metric ton corncob dry matter. The cost of the minimum usage of ammonia was 3.4 cents per liter of anhydrous alcohol. Starting fermentation at pH 5.9 leads to an increase of 0.5 cents per liter of anhydrous alcohol, compared to a fermentation starting at pH 5.3.

Table 3 shows that fermentation time increases with a decrease in commercial yeast nutrient load (source of yeast assimilable nitrogen from protein). Yeast growth and viability requires organic and inorganic nitrogen sources, as discussed above.

Figure 3:
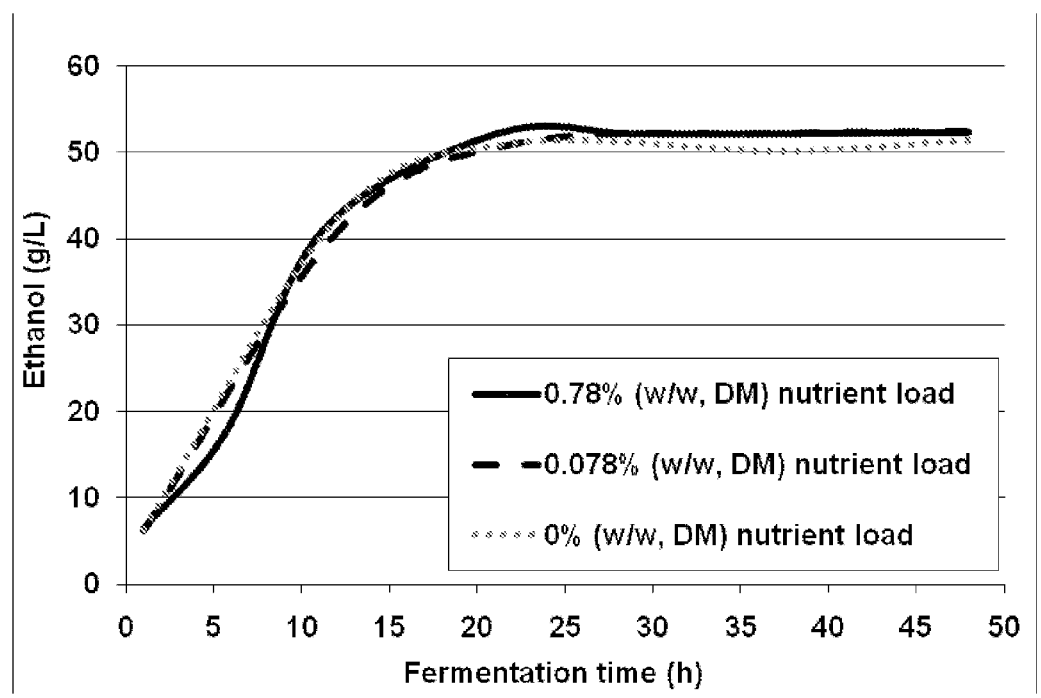
FIG. 3 shows the effect of yeast commercial nutrient load on the fermentability of unwashed, undetoxified corncob hydrolysate from steam explosion pretreatment, when the fermentation is carried out at a high load of pH adjustment chemical (pH 5.9)

Table 4 shows that alternative yeast nutrients from a corn ethanol plant can replace commercial yeast nutrients. The main nitrogen source in commercially available yeast nutrients is protein. The percentage of protein in Goferm is 51.4% (w/w, DM). FIG. 3 shows that the fermentation of pretreated corncobs can be performed with no nutrient addition if the pH is raised to 5.9 with the use of high load of preferred pH adjustment chemical. These results were anticipated since ammonia usage to reach higher pH prior fermentation was significantly greater and ammonia is also widely used as inorganic nitrogen source for yeast growth.

Figure 4:
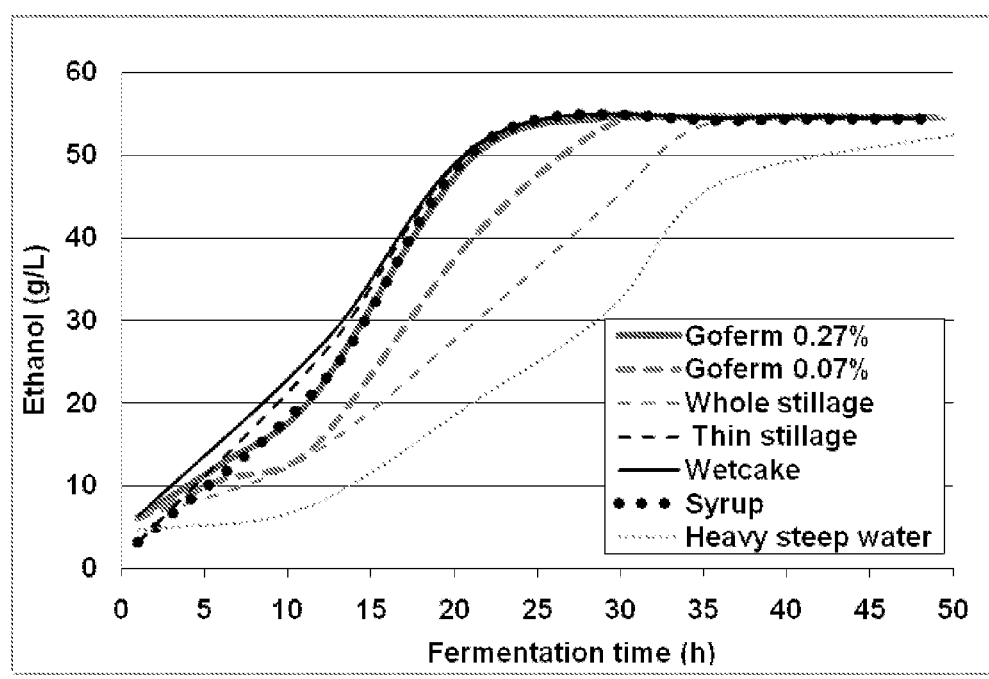
FIG. 4 shows the effect of nutrient sources on the fermentability of unwashed, undetoxified corncob hydrolysate from steam gun pretreatment when the fermentation are carried out at a low load of pH adjustment chemical (pH 5.3).

FIG. 4 shows that side streams or stillage residuess from a starch to ethanol facility can be successfully used as alternative source of yeast nutrient and allow operation of the fermentation process at pH 5.3, and at the lowest possible input of pH adjustment chemical.

Table 5 shows that fermentation rates and yields obtained with the addition of wet cake, thin stillage and syrup as nutrients, were similar to those obtained with the yeast commercial yeast nutrient. The use of syrup as yeast nutrient for the fermentation of pretreated corncob hydrolysate is recommended since syrup is the final by-product of the starch to ethanol process. Moreover, only a part of the syrup produced is normally sold at low cost ($20 per/MT as is). Disposal of the remaining syrup is a significant process issue.

The stillage residues have, among other things, protein, triglycerides, free fatty acids, vitamins, sterols, etc. that help the yeast ferment. While soluble protein is a more favorable nutrient for yeast, the whole stillage contains both soluble and insoluble protein. The thin stillage and subsequent syrup contain a greater concentration of soluble protein than the whole stillage. As can be seen in Table 5, the protein load of the wet cake is 50% more than that of the stillage and the syrup, and the addition of wet cake as a nutrient source achieves 90% fermentation in the same amount of time as the when the stillage or the syrup are used as a nutrient source. It can also be seen from Table 5 that the whole stillage has equal protein to that of the Goferm load 2; however when the whole stillage was used as a nutrient source, it took longer to reach 90% fermentation than when the Goferm load 2 was used as a nutrient source. This is likely due to the high level of insoluble protein in the whole stillage as compared to that of the expensive Goferm. The Heavy Steep Water is a special case as it had a slightly higher load of soluble protein over the syrup but gave the worst result. This is likely due to the very high content of lactic acid 10% w/v and acetic acid 0.4% w/v as seen in Table 4b.

EXAMPLE 2

Batch steam explosion corncob pretreatment was carried out in a steam gun treatment process and experimental cellulose pretreatment setup as described in U.S. Provisional Patent Application No. 61/097,692—Cellulose pretreatment process.

Batch loads of 6 kg DM of 0.5 to 1 cm corncob were used per steam explosion shot. Pressurized saturated steam at temperatures of 190 to 210 degrees C. was fed into the steam gun until the desired cooking pressure was reached. Cooking pressures of 235 psig were used. After a residence time of 8 minutes, the pressure in the steam gun was quickly released. Complete pressure relief was achieved in 600 to 1000 ms. During the residence time and prior to pressure release, condensate and cooking liquids collected at the bottom of the steam gun were purged through purge discharge control. Solids and gaseous reaction products ejected from the steam gun on pressure release were separated in a cyclone separator. The solids collected at the bottom of cyclone separator were subjected to lab scale hydrolysis and fermentation.

Carbohydrate composition analysis of corncobs as fed and corncob prehydrolysates collected at the bottom of the cyclone separator was carried out at Paprican's analytical laboratory (Montreal, Qc).

Complete enzymatic digestion of corncob pre-hydrolysates was carried out with a commercial enzyme product GC220 (Genencor) at a medium consistency of the corncob prehydrolysate (25%), 3.0% load of enzyme (w/w, DM), 50° C., and pH 5.0 in a 1-Liter stirred reaction vessel (150 rpm). pH was adjusted with aqua ammonia (15%, w/w).

Fermentations were carried out using Ethanol Red, a commercial industrial grade C6-fermenting yeast from Fermentis. Yeast inoculation was carried out by adding 6.67 g dry yeast per kilogram of corncob hydrolysates leading to an average yeast population of $10^8$ cells/ml hydrolysate after rehydration.

Fermentation experiments were carried out in 1-liter beakers at 35° C., pH 5.3, using 13.5 g as-is of syrup from a corn starch-to-ethanol dry mill process. pH adjustment of unwashed, undetoxified hydrolyzed corncob prehydrolysate was carried out prior to fermentation, using different quantities of aqueous ammonia (30%, w/w).

The key parameters used were fermentation rates and yield. Fermentation rates and yield of batch or continuous steam explosion pretreated corncob were assessed with respect to the usage of pH adjustment chemical and yeast nutrient needs.

Glucose, xylose, ethanol, glycerol and carboxylic acid concentrations were determined by HPLC analysis. Quantification of soluble products from pretreatment, enzymatic hydrolysis and fermentation was carried out by HPLC analysis. Target molecules were monitored to determine the relative contents of cellulose and downstream inhibitors in the prehydrolysate obtained. The target molecules were sugar monomers such as glucose and xylose as well as toxic compounds such as different carboxylic acids, namely acetic acid, succinic acid and lactic acid and degradation products of carbohydrates such as glycerol, HMF and furfural as well as ethanol.

TABLE 1

| pH[1] | 5.0 | 5.2 | 5.3 | 5.6 | 5.9 |
|---|---|---|---|---|---|
| Time 90%[2] (h) | NA[3] | 24 | 19 | 17 | 15 |

[1]Fermentation pH
[2]Time to reach 90% of the maximum glucose to ethanol conversion
[3]Not applicable (%-conversion never reached)

TABLE 2A

| | | pH 5.9 | pH 5.3 |
|---|---|---|---|
| (A) | Volume (ml) 30% ammonia per kg DM corn cob | | |
| | Hydrolysis | 51 | 51 |
| | Saccharification | 8 | 8 |
| | Fermentation | 20 | 10 |
| | Total | 79 | 69 |
| (B) | Cent per Liter anhydrous alcohol | | |
| | Hydrolysis | 2.5 | 2.5 |
| | Saccharification | 0.4 | 0.4 |
| | Fermentation | 1.0 | 0.5 |
| | Total | 3.9 | 3.4 |

TABLE 3

| Goferm g-as is/kg | Goferm load (%, w/w, DM) | Protein load (%, w/w, DM) | Time 90% (h) |
|---|---|---|---|
| 8.3 | 0.78 | 0.4 | 20 |
| 5.6 | 0.52 | 0.27 | 23 |
| 2.8 | 0.26 | 0.13 | 24 |
| 1.3 | 0.13 | 0.07 | 28 |
| 0.0 | 0.0 | 0.0 | 49.0 |

TABLE 4

(A)

| Nutrient sources | % Dry Matter | % Crude Protein | % Crude Fat |
|---|---|---|---|
| Goferm | 93.7 | 51.4 | 0.6 |
| Wetcake | 32.9 | 36.6 | 8.4 |
| Thin stillage | 7.6 | 22.8 | 18.7 |
| Syrup | 33.7 | 20.9 | 19.8 |
| Whole stillage | 12.7 | 30.8 | 14.2 |
| Heavy steep water | 42.3 | 49.2 | 0.3 |

(B)

| | Soluble compounds concentration (g/L) | | | | |
|---|---|---|---|---|---|
| Nutrient sources | Glucose | Xylose | Lactic acid | Glycerol | Acetic acid |
| Wetcake | 0.00 | 0.43 | 1.49 | 8.62 | 0.74 |
| Thin stillage | 0.10 | 0.59 | 1.96 | 12.69 | 0.36 |
| Syrup | 1.25 | 2.94 | 8.91 | 61.31 | 0.50 |
| Whole stillage | 0.00 | 0.32 | 5.48 | 12.63 | 0.44 |
| Heavy steep water | 42.54 | 44.94 | 96.13 | 3.99 | 4.26 |

TABLE 5

Nutrient sources, loads and impact on fermentation rates

| Nutrient sources | Nutrient load (g) as is per kg | Protein load (%, w/w, DM) | Time 90% (h) |
|---|---|---|---|
| Goferm load1 | 5.6 | 0.27 | 21 |
| Goferm load2 | 1.3 | 0.07 | 28 |
| Wetcake | 12.4 | 0.15 | 21 |
| Thin stillage | 60.0 | 0.10 | 21 |
| Syrup | 13.5 | 0.10 | 21 |
| Whole stillage | 17.0 | 0.07 | 32 |
| Heavy steep water | 5.4 | 0.11 | 40 |

What is claimed is:

1. A process for the production of cellulosic ethanol from lignocellulosic biomass, comprising the steps of:
    Pretreating the lignocellulosic biomass to decompose the lignocellulosic biomass into fibrous solids;
    Hydrolyzing the fibrous solids with enzymes to produce cellulose sugars; and
    fermentating the cellulose sugars in the presence of a stillage residue from a whole grain starch-to-ethanol dry mill process,
    wherein the step of pretreating the lignocellulosic biomass includes process conditions including the step of exposing the lignocellulosic biomass to steam in a reaction vessel at an elevated temperature and reaction pressure for a preselected exposure time, and releasing the reaction pressure for explosive decomposition of the lignocellulosic biomass,
    wherein the process conditions are selected for the achievement of a severity index of 3.9 to 4.1.

2. The process of claim 1, wherein the stillage residue is selected from the group consisting of whole stillage, thin stillage, wetcake, syrup, and any combination thereof.

3. The process of claim 1, wherein the elevated temperature is in the range of 190-210° Celsius, the reaction pressure is between 190 to 275 psig, and the preselected exposure time is between 3 to 10 minutes.

4. The process of claim 1, wherein the elevated temperature is 205 degrees Celsius, the reaction pressure is 235 psig, and the preselected exposure time is 8 minutes.

5. The process of claim 3, wherein the pressure is released within less than 1000 milliseconds.

6. The process of claim 3, wherein the pressure is released within 300 milliseconds.

7. The process of claim 1, wherein the severity index is 4.0.

8. The process of claim 1, wherein the enzymatic hydrolysis is carried out at 10-30% consistency, and at a temperature of 40-60° Celsius and a pH 4.5 to 5.5.

9. The process of claim 1, wherein the fermentation step is carried out at 10-30% consistency, 30-37° C. and a pH of 5.2 to 5.9.

10. The process of claim 1, wherein the enzymatic hydrolysis of solids is carried out at a temperature of 50° C., pH 5.0 until completion.

11. The process of claim 1, wherein the fermentation step is carried out at a temperature of 35° C., and at a pH of 5.3 until completion.

12. The process of claim 1, further comprising a process arrangement step for step of collecting and processing fermentation products for distilling fuel grade ethanol.

13. The process of claim 12, wherein the process arrangement step for distilling fuel grade ethanol includes a distillation portion, a condensation and dehydration portion, a separation and drying portion and an evaporation portion.

14. The process of claim 13, wherein the process arrangement produces hot ethanol vapor and thin stillage.

* * * * *